United States Patent [19]
Aikus et al.

[11] Patent Number: 5,603,894
[45] Date of Patent: Feb. 18, 1997

[54] METHOD OF STERILIZING A PHARMACEUTICAL COMPOSITION

[75] Inventors: Albert J. Aikus, Lake Villa; Joaquin Mayoral, Downers Grove, both of Ill.

[73] Assignee: Abbott Laboratories, Abbott Park, Ill.

[21] Appl. No.: 332,191

[22] Filed: Oct. 31, 1994

[51] Int. Cl.⁶ .............................. A61L 2/04; A23L 3/005
[52] U.S. Cl. .................. 422/23; 422/38; 422/111; 422/308; 426/521; 99/483
[58] Field of Search .................. 422/21, 23, 26, 422/38, 307, 308, 109, 111; 426/521, 599; 99/483

[56] References Cited

U.S. PATENT DOCUMENTS

| | | | |
|---|---|---|---|
| 4,534,986 | 8/1985 | Hasting | 426/599 X |
| 4,990,347 | 2/1991 | Rasmussen et al. | 426/232 |
| 4,994,291 | 2/1991 | Swartzel et al. | 426/399 |

*Primary Examiner*—Robert J. Warden
*Assistant Examiner*—E. Leigh Dawson
*Attorney, Agent, or Firm*—Brian R. Woodworth

[57] ABSTRACT

The present invention provides a method and apparatus for sterilizing a pharmaceutical composition, the method comprising providing a sterilization system including a heat exchanger for elevating and then lowering the temperature of the fluid in a time period; measuring temperature at an input of the heat exchanger, measuring temperature at an output of the heat exchanger and measuring temperature at least one point in the heat exchanger intermediate to the input and output; calculating a coefficient of heat transfer for the sterilization system using the temperature measurements; calculating a degree of sterilization ($F_o$) using the coefficient; and adjusting the temperature of the heat exchanger to minimize degradation of the pharmaceutical composition while maintaining an acceptable degree of sterilization.

8 Claims, 2 Drawing Sheets

METHOD OF STERILIZING A PHARMACEUTICAL COMPOSITION

TECHNICAL FIELD OF THE INVENTION

This invention relates to a method of sterilizing a pharmaceutical composition. More particularly, this invention relates to a method of sterilizing a pharmaceutical composition by heating the composition to an elevated temperature for a short period of time wherein the temperature and time required to obtain the desired degree of sterilization are calculated and adjusted so that thermal degradation of the pharmaceutical composition is minimized.

BACKGROUND OF THE INVENTION

Pharmaceutical compositions that contain pharmaceutically active compounds, such as drugs and vitamins, or other pharmaceutical compositions, such as fluids to be delivered to a patient intravenously, must be sterilized to prevent the patient who is receiving such a pharmaceutical composition from becoming infected with microorganisms, such as bacteria, and to prevent spoilage of the pharmaceutical composition.

One common method of sterilizing a pharmaceutical composition is by heating the composition to kill any microorganisms. However, many pharmaceutically active compounds are destroyed or degraded when exposed to heat. In general, the higher the temperature, the more the composition degrades. Similarly, the longer the composition is exposed to heat, the more the composition degrades. A method that has been used to sterilize compositions that are relatively insensitive to heat degradation is to place those compositions in an autoclave, which heats the compositions. In addition to not being suitable for compositions that are heat sensitive, autoclaving is usually carried out terminally; that is, after the bulk composition has been prepared, filled and sealed in the final container, which can be inefficient and time consuming. Also, the elevated temperatures associated with autoclaving promote undesirable chemical reactions between the pharmaceutical composition and the container or its component parts.

Because many pharmaceutical compositions are heat sensitive, autoclaving such compositions is not possible. Instead, a heat sensitive composition, if in the form of a solution, may be filtered so that any harmful microorganisms are removed from the solution. However, filtering can be a costly process and cannot be used to sterilize pharmaceutical compositions that are not true solutions, such as mixtures and suspensions. Moreover, sterilization by filtration is very difficult if the solution has a high viscosity.

Another sterilization process that does not employ heat is radiation sterilization. In this process of sterilization, a composition to be sterilized is irradiated with certain types of radiation, which can include high-energy particles as well as portions of the electromagnetic spectrum. Again, however, many pharmaceutical compositions cannot be sterilized by radiation because irradiation of such pharmaceutical compositions destroys or degrades the compositions or the containers in which the compositions are stored.

Chemicals have also been used to sterilize compositions. Such chemicals are typically antibacterial substances. However, the addition of such chemicals to a pharmaceutical composition may not be desired, as the chemicals may be detrimental to the patient to whom the pharmaceutical composition is to be administered or may be detrimental to any of the various components of a pharmaceutical composition. Moreover, such chemicals, at low concentrations, can be bacteriostatic rather than bactericidal; that is, they prevent the growth of bacteria, but may not kill them.

A sterilization method for sterilizing pharmaceutical compositions using heat that does not result in unacceptable degradation of the pharmaceutical composition is provided by the present invention.

The invention is a method of controlling the degree of degradation of a heat sensitive pharmaceutical composition by quantification and control of the thermal input required to sterilize the composition.

SUMMARY OF THE INVENTION

The present invention provides a method of sterilizing a pharmaceutical composition, the method comprising providing a sterilization system including heat exchanger means for elevating and then lowering the temperature of the fluid in a time period; measuring temperature at an input of the heat exchanger means, measuring temperature at an output of the heat exchanger means and measuring temperature at one or more points in the heat exchanger means intermediate to the input and output; calculating a coefficient of heat transfer for the sterilization system using the temperature measurements; calculating a degree of sterilization ($F_o$) using the coefficient; and adjusting the temperature of the heat exchanger means to minimize degradation of the pharmaceutical composition while maintaining an acceptable degree of sterilization.

In a preferred embodiment, the method includes calculating the coefficient of heat transfer for a plurality of flow rates and/or temperatures.

DETAILED DESCRIPTION OF THE PREFERRED EMBODIMENTS

This invention provides a method of sterilizing a pharmaceutical composition by heating the composition to a high temperature for a short period of time wherein the temperature and time required to obtain the desired degree of sterilization (Fo) are calculated and adjusted so that thermal degradation of the pharmaceutical composition is minimized.

In other words, the present invention provides a method of quantifying the thermal input to a pharmaceutical composition as the composition traverses the sterilization system and, in particular, the heat exchanger means. The desired degree of sterilization of the pharmaceutical composition is achieved by controlling the thermal input to the composition.

It is possible to sterilize a heat sensitive composition by heating the composition to a temperature and then cooling the composition quickly so that the composition resides at the high temperature for only a very short time because the kinetics of microorganism inactivation are first-order (log linear), whereas thermal chemical degradation kinetics are zero-order (linear).

The present method of sterilization of a pharmaceutical composition comprises providing a sterilization system, which includes a source of the pharmaceutical composition, heat exchanger means, which can be used to rapidly heat and rapidly cool the pharmaceutical composition, and various temperature sensing means, which can be used to measure the temperature of the pharmaceutical composition at various points in the sterilization system; calculating the coefficient of heat transfer for the particular sterilization system, including the pharmaceutical composition; calculating the degree of sterility (Fo) using the coefficient and adjusting the temperature of the heat exchangers and/or the flow rate of the pharmaceutical composition to minimize degradation of the composition while allowing for the desired degree of sterilization to be obtained.

As used herein, a "pharmaceutical composition" shall include, but is not limited to, a fluid that contains a pharmaceutically active compound such as a drug, hormone, peptide, nucleotide, antibody, protein, vitamin, or saccharide. Moreover, the term pharmaceutical composition shall include parenteral solutions and fluids that are administered to a patient intravenously, such as glucose or sodium chloride solutions and any other solution for which sterilization is desired before the solution is administered to a patient. As used herein, the term "patient" shall include humans and animals.

Figure 1:
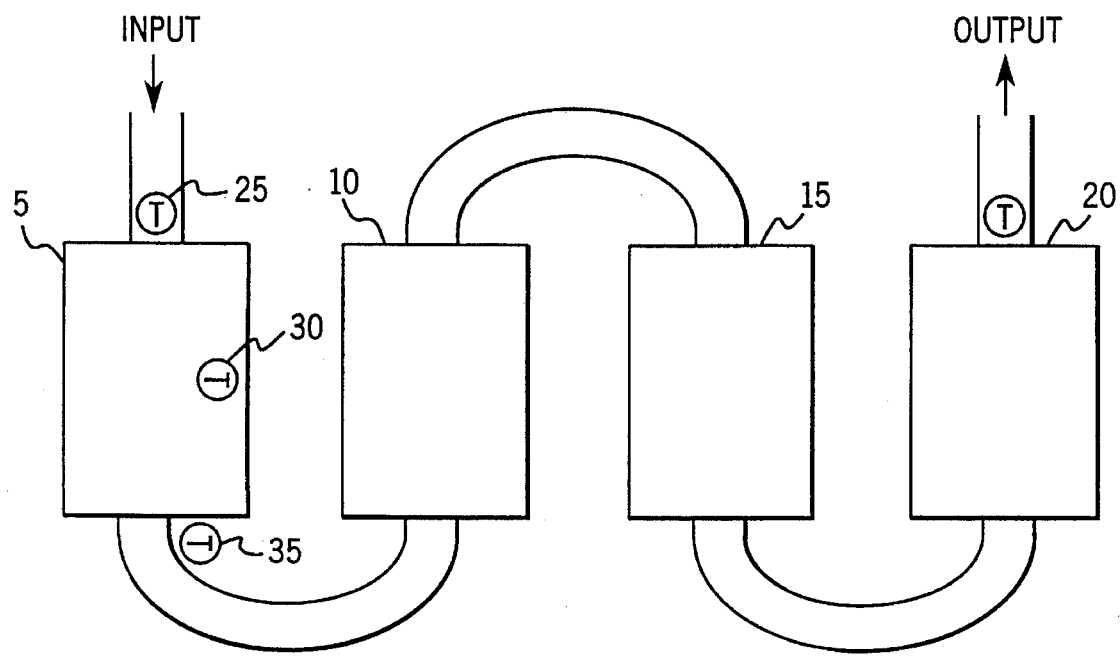
FIG. 1 is a diagram of a sterilization system useful in the present invention.

FIG. 1 is a diagram of an exemplary sterilization system. The elements labeled 5, 10, 15 and 20 are heat exchanger means, with 5 and 10 being heating means and 15 and 20 being cooling means. Elements 25, 30 and 35 are temperature sensing means. In practice, a sterilization system for practicing the present invention can include a greater number or a lesser number of heat exchangers and associated valves, and the like for operational control.

The heat exchanger means may comprise any device that is known to those skilled in the art that can increase or decrease the temperature of a solution. For example, the heat exchanger may use steam, radiant energy, or electrical energy (resistive heating) to heat a pharmaceutical composition. Alternatively, to cool a pharmaceutical composition, the composition can be passed through a heat exchanger that contains cool tap water or some other cooling medium. Heat exchanger means are known to those skilled in the art, and it is contemplated that any of the various heat exchanger means may be employed in the present invention. Moreover, it is contemplated that a plurality of heat exchanger means may be used in series to obtain the heating and cooling profile desired. For example, the sterilization system can comprise four heat exchanger means, where two adjacent heat exchangers are used for heating the solution and two adjacent heat exchangers are used to cool the solution. It is also recognized that many other configurations exist and that all these heat exchanger configurations are contemplated as falling within the scope of this invention.

Temperature sensing means are also well known to those skilled in the art, and it is contemplated that any temperature sensing means that can be used to measure the temperature of the pharmaceutical composition may be used. Preferably, the temperature sensing means is a Type T thermocouple. It is also preferable that the temperature sensing means has the ability to introduce temperature data directly into a computer. More preferably, the temperature sensing means should have the ability to introduce temperature data continuously into a computer. Preferably, the temperature sensing means are located in the entrance and the exit to the heat exchanging means and in at least one point in the heat exchanging means (i.e., the temperature sensing means such as a thermocouple is positioned to sense temperature at the center tube of the heat exchanger).

The pharmaceutical composition is introduced into the sterilization system by means of a pump. The pump may have a means for controlling the flow rate of the pharmaceutical composition through the sterilization system. However, the sterilization system may also include various other means for controlling the flow of the pharmaceutical composition through the sterilization system. For example, the flow of the pharmaceutical composition may be controlled using valves.

The flow rate of the pharmaceutical composition may be measured using the various methods known in the art. In particular, the flow rate of the pharmaceutical composition is measured as the composition passes through the heat exchanger means. It is also desirable to introduce flow rate data directly and continuously into a computer.

The temperature and flow rate of the pharmaceutical composition that yields an acceptable degree of sterilization while minimizing any degradation of the pharmaceutical composition may be calculated using the temperature data obtained by the temperature sensing means of the sterilization system.

$Fo_{phys}$ is a measure of the temperature induced microorganism kill rate and is defined as the equivalent time at a reference temperature of 121° C. for the purpose of defining rate of sterilization. Fo has been defined by experimentation in autoclaves. To obtain a particular level of kill, the pharmaceutical composition must be subjected to an appropriate total or cumulative $F_o$. In general, Fo should be greater than 6, and preferably, Fo is greater than 8. Just as the microbial kill increases at elevated temperatures (greater than about 120° C.), thermal chemical degradation of heat sensitive compounds also proceeds at accelerated rates, which can be predicted for many types of degradation reactions by the Arrhenius equation. The Arrhenius equation, which is well known, gives the relationship between the rate of a chemical reaction and temperature. Here, the chemical reaction of interest is the degradation reaction of a heat sensitive compound when the compound is exposed to heat.

Theoretically, two basic pieces of information are needed to predict microbial kill and the extent of thermally induced chemical degradation: time and temperature.

Figure 2:
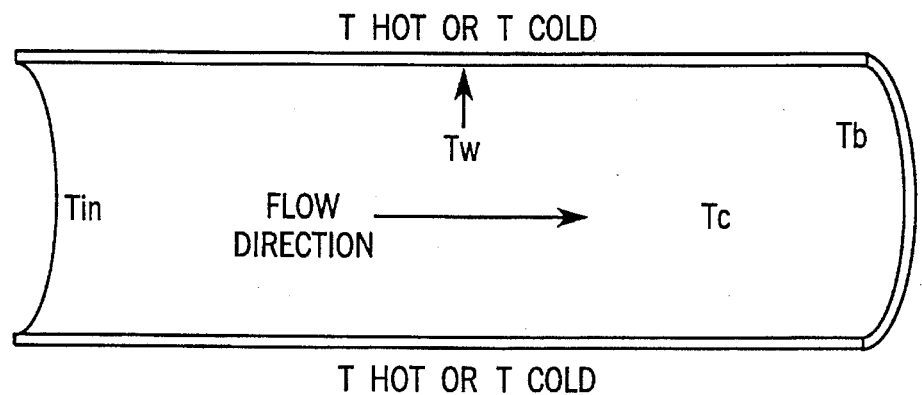
FIG. 2 shows a cross-sectional representation of a flow path for a pharmaceutical composition within a heat exchanger.

FIG. 2 shows a cross-sectional representation of a tube running through a heat exchanger in a sterilization system. For a steady state flow of a pharmaceutical composition through the sterilization system, Tb(x) is the local bulk (mean or mixing cup) temperature at x. x is the distance from the heat exchanger entrance to any point in the pipe that runs through the heat exchanger. Tin is the temperature of the pharmaceutical composition as it enters the heat exchanger. Tw is the temperature at the inner wall of the tube. Tc is the temperature at the center of the tube and is the coldest temperature in the tube. At any x, the bulk temperature and the coldest temperature are related by the following relationship $$\frac{Tb(x) - Tw}{Tc(x) - Tw} = \frac{2n+1}{2(n+2)} \quad (1)$$

where n=6.6 for Reynolds (Re) number 23,000 and n=7.0 for Re=110,000.

Then:

$$\frac{Tb(x) - Tw}{Tc(x) - Tw} = 0.826 \text{ and } 0.833 \text{ (avg = 0.83)} \quad (2)$$

The heat transfer coefficient for flow inside a tube is independent of x once x/D>10 according to classic flow theory. For the case when x/D>10, and for Tw=constant (a good approximation for steam), the classic heat transfer equation gives:

$$\frac{Tb(x) - Tw}{Tin - Tw} = e^{\frac{h \cdot \pi \cdot D \cdot x}{m \cdot Cp}} \quad (3)$$

where m is the mass flow rate and Cp is the specific heat of the pharmaceutical composition. This equation can also be transformed into dimensionless parameters by using the approximate definitions and substitution to:

$$\frac{Tb(x) - Tw}{Tin - Tw} = e^{\frac{Nu}{RePr}(4\frac{x}{D})} \quad (4)$$

Nu=Nusselt number, Re=Reynolds number and Pr=Prandtl number. The ratio of Nu/RePr is also known in the field of heat transfer as the Stanton number.

Solving equation (2) for Tb(x) in terms of Tc(x) then substituting into equation (4), gives:

$$0.83 \cdot \frac{Tc(x) - Tw}{Tin - Tw} = e^{\frac{Nu}{RePr}(4\frac{x}{D})} \quad (5)$$

solve for Tc (x):

$$Tc(x) = Tw + \frac{Tin - Tw}{0.83} \cdot e^{\frac{Nu}{RePr}(4\frac{x}{D})} \quad (6)$$

or from equation 4 solve for Tb(x):

$$Tb(x) = Tw + (Tin - Tw) \cdot e^{-\frac{Nu}{RePr}(4\frac{x}{D})} \quad (7)$$

The expression Nu/RePr can be calculated from the Petukhov-Popov equation, valid for Re greater than or equal to 10,000.

$$\frac{Nu}{Re \cdot Pr} = \frac{f/8}{1.07 + 12.7 \cdot (Pr^{2/3} - 1) \cdot \sqrt{f/8}} \quad (8)$$

and where f, the friction factor is:

$$f = \frac{1}{(1.82 \cdot \log_{10} Re - 1.64)^2} \quad (9)$$

To simplify analysis, the natural log of both sides of equation (4) is:

$$\text{Ln}\left(\frac{Tb(x) - Tw}{Tin - Tw}\right) = -\frac{Nu}{RePr}\left(4\frac{x}{D}\right) \quad (10)$$

In this equation Tb(x) and x are variables and 4, D, Re, Nu and Pr represent interrelated constants for the flow regimes of interest. Thus, the equation (10) can be further rearranged to:

$$\text{Ln}\left(\frac{Tb(x) - Tw}{Tin - Tw}\right) = -\frac{Nu \cdot 4}{RePr} \cdot \left(\frac{x}{D}\right) \quad (11)$$

The above mathematical representation provides a general framework from which the following mathematical models of heat input maybe derived. Recognizing equation (11) as a simple linear relationship, a single constant can be substituted for the multiplier of x/D.

$$\text{Ln}\left(\frac{Tb(x) - Tw}{Tin - Tw}\right) = A \cdot \left(\frac{x}{D}\right) \quad (12)$$

Figure 3:
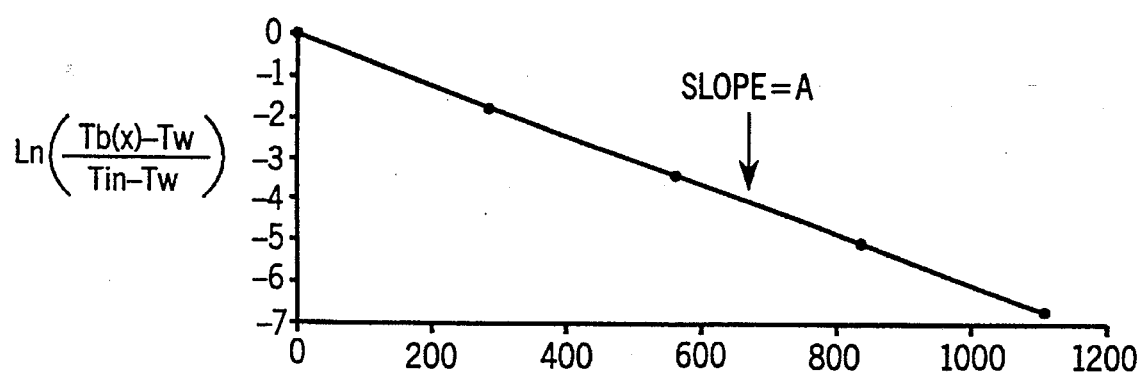
FIG. 3 is a plot of $Ln(Tb(x)-Tw/Tin-Tw)$ versus $x/D$.

Equations 11 and 12 both show that the relationship between $T_b$ and x is linear and has a y intercept on the Ln(Tb(x)–Tw/Tin–Tw axis at zero. The zero crossing can be proven by observing that for the given equation at x=0, Tb=Tin, the quotient within the parenthesis=1, i.e., log of 1=0. This mathematical fact simplifies the linear regression analysis which may be used to predict the value of A (or the slope of the line obtained) for the system by allowing the use of a so-called forced zero regression analysis. The forced zero regression analysis differed from a regular regression analysis by assuming that the y intercept is zero. It also simplifies the characterization of the heating process by allowing it to be described by only one constant, the slope (A). An exemplary plot of Ln(Tb(x)–Tw/Tin–Tw) versus x/D is shown in FIG. 3. A single constant is much simpler to analyze that the two independent constants (slope and y intercept) normally calculated in a linear regression. In this case, regression analysis of A to flow or Re may provide for prediction of A for different flow rates without having to to each one separately. If A can be predicted, then the number and size of heat exchangers required for any sterilization system may be determined.

Proceeding from equation (12), a method to calculate Fo accumulation in the heat up section of the sterilization system has been determined. Theoretically, the development of the method starts with bulk temperature profile equations and then proceeds from there to apply the results to Fo cumulative using Fo physical. Unless otherwise defined, Fo shall mean Fo cumulative.

Fo physical is defined as:

$$Fo(T) = 10^{\left(\frac{T - Tref}{z}\right)} \cdot \min^{-1} \quad (13)$$

Equation 13 shows that $F_o$ does not accumulate appreciably until T reaches Tref. The Tref in this case is 121.11° C., and z is 10. As can be seen if Tb is substituted for T, Fo physical can be calculated for any point defined by the equation for Tb. If in addition the time at a particular temperature is known, the cumulative Fo can be calculated for that period of time.

$$F_{Cumulative} = Fo(Tb(x)) \cdot \text{Time} \quad (14)$$

In the present sterilization system both are known. However, because the temperature is changing with x especially during initial heat up, the temperature at a particular time period can vary dramatically. To better account for the contribution of the heat rise, the heat up tube can be segmented mathematically into small pieces of length delx. The predicted temperature of each piece can then be used to calculate Fo. This Fo value is multiplied by the time required to traverse the piece, delt, to get the cumulative Fo for that piece. Writing this down in mathematical short hand and summing all the pieces together gives:

$$F_{Cumulative} = \sum_{x=0, delx, 2-delx, etc.}^{L} Fo(Tb(x)) \cdot delt \quad (15)$$

If delt is allowed to get very small and we change L to its corresponding time parameter, the following integral is obtained:

$$F_{Cumulative} = \int_0^{} Fo(Tb(t)) \cdot dt \quad (16)$$

both equation 15 and 16 can be used to predict the cumulative Fo.

Application of these equations directly is complicated by the fact that Tw is not known and that the sterilization system may be segmented into multiple heat exchangers. These difficulties can be partially overcome if one assumes that the bulk temperature will eventually equilibrate close to Tw. Thus, taking the temperature at the end of a long heat exchanger series is a good approximation of Tw. For shorter heat exchange assemblies that do not reach equilibrium, one should be able to fit the available data to a linear model by iterative methods. Both methods require that one know the bulk or coldest temperature accurately at the exit and entrance to the heat exchangers.

In equation 10, Tb(x) is the bulk temperature of the pharmaceutical composition at position x in the heat exchanger. Tin is the bulk temperature of the pharmaceutical composition at the entrance to the heat exchanger. Both temperatures can be measured directly by a temperature sensing means such as a thermocouple, if the fluid is well mixed. Tw is the temperature of the inner surface of the heat exchanger tube, which is driving the increase or decrease in temperature of the pharmaceutical composition as the composition moves through the heat exchanger. The expression x/D is the distance down the heat exchanger divided by the internal diameter of the tube which contains the pharmaceutical composition. x is divided by D to make it a nondimensional variable. The Stanton coefficient or Nu/RePr is an average of the heat transfer properties of the fluid in a nondimensionalized form from the inner wall of the inward along the length of the tube evaluated. The Stanton coefficient can be estimated by performing the regression analysis explained above to obtain the slope A of the line obtained, which herein is called the coefficient of heat transfer. Preferably, the coefficient of heat transfer is calculated using two or more temperature measurements.

A model sterilization system having two steam driven heat exchangers for raising the temperature of the composition followed by two heat exchangers using tap water to cool the composition and elbow shaped interconnecting tubes between each heat exchanger may be considered.

The first steam heated heat exchanger (length=L) heats the composition from room temperature to some large fraction of the wall temperature (Tout 1=fraction *Tw). This heat exchanger produces the most profound change in temperature on the composition. Assuming Tw is a constant, the following conditions are theoretically predicted:

at x=0, Tb(0)=Tin, Ln((Tb(0)−Tw)/(Tin−Tw)=Ln((Tin−Tw)/(Tin−Tw))=0=−(Nu/RePr)*4*0/D at x=L, Tb(L)=Tout 1, Ln((Tout 1−Tw)/(Tin−Tw))=−(Nu/RePr)*4*L/D Tin, Tout 1, L and D are measurable quantities. Tw and −(Nu/RePr)*4 are unknown. In addition, Tw and −(Nu/RePr)*4 are directly dependent on each other because the Reynolds number is calculated from viscosity and density, both of which are temperature dependent. Tw can be no more that the steam temperature. There are two methods of obtaining the value for Tw. One requires the special placement of a thermocouple to measure Tw directly, as is known in the art. The other method involves estimating Tw from bulk temperature measurements.

The initial method used to estimate Tw using bulk temperature measurements is to observe the maximum steady state temperature achieved by the composition as it passes through the heat exchanger sections. This approach assumes that the drug eventually equilibrates to Tw. This method fails if there is a need to terminate the heating process before the temperature equilibrates because Tb can not approach Tw during the chosen sterilization cycle. An indirect approach to obtain an estimate for this case would be to run experimental trials at the same conditions with added heat exchanger sections to find what Tw should have been. This method can also fail if there is cooling between the exit of one heat exchanger and the entrance of the next. Under these conditions true Tw may never be reached.

Tw can also be calculated by substituting measured entrance and exit temperatures into a theoretical equation. The theoretical relationship given in equation 4 above may be used if there is one large heat exchanger or if there is a series smaller of heat exchangers. Given a constant Tw and Tin, the Tb(x) will rise according to the magnitude of−(Nu/RePr)*4 and x. For the same set of conditions, the coefficient−(Nu/RePr)*4 is the same for one large heat exchanger as for a series of heat exchangers with the same overall length. Thus, theoretically, if the heat exchanger is split into two interconnected pieces the same coefficient applies to each segment.

The first heat exchanger of length L gives:

$$\text{Ln}\left(\frac{Tb(L)-Tw}{Tin-Tw}\right) = \left(-\frac{Nu}{RePr}\cdot 4\right)\cdot\frac{L}{D} \quad (17)$$

The second heat exchanger gives:

$$\text{Ln}\left(\frac{Tb(2L)-Tw}{Tin-Tw}\right) = \left(-\frac{Nu}{RePr}\cdot 4\right)\cdot\frac{2L}{D} \quad (18)$$

or $$\frac{1}{2}\text{Ln}\left(\frac{Tb(2L)-Tw}{Tin-Tw}\right) = \left(-\frac{Nu}{RePr}\cdot 4\right)\cdot\frac{L}{D} \quad (19)$$

Therefore equating the left hand sides of equations 17 and 19 gives:

$$\text{Ln}\left(\frac{Tb(L)-Tw}{Tin-Tw}\right) = \frac{1}{2}\text{Ln}\left(\frac{Tb(2L)-Tw}{Tin-Tw}\right) \quad (20)$$

or $$2\cdot\text{Ln}\left(\frac{Tb(L)-Tw}{Tin-Tw}\right) = \text{Ln}\left(\frac{Tb(2L)-Tw}{Tin-Tw}\right) \quad (21)$$

$$\text{Ln}\left(\left(\frac{Tb(L)-Tw}{Tin-Tw}\right)^2\right) = \text{Ln}\left(\frac{Tb(2L)-Tw}{Tin-Tw}\right) \quad (22)$$

Raising e to the value of each side gives:

$$\left(\frac{Tb(L)-Tw}{Tin-Tw}\right)^2 = \left(\frac{Tb(2L)-Tw}{Tin-Tw}\right) \quad (23)$$

TW is therefore:

$$Tw = \frac{T(L)^2 - Tin\cdot T(2L)}{2T(L) - Tin - T(2L)} \quad (24)$$

This method gives the most theoretically sound estimate of Tw. The estimate is only as good as the temperature measurements in the system and to the extent the mathematical model reflects the system. The extent the mathematical model reflects the system can be checked by applying formula (24) to succeeding triumvariates, i.e., T(L); T(2L); T(3L) and T(2L); T(3L); T(4L). The resultant Tw's should match closely.

Now that a theoretical method of estimating Tw is provided, a plot of the quantity Ln((Tb−Tw)/(Tin−Tw)) for exit temperatures at L,2*L, etc., may be made, from which one can obtain the magnitude of−(Nu/RePr)*4, either graphically or by linear regression analysis.

Estimates of Fo may be based on regressions made from the temperatures recorded within the connecting tubes. Once the coefficient−(Nu/RePr)*4 is calculated, Tb could be predicted at any x. The next step is to calculate the cumulative Fo.

The cumulative Fo is required to estimate the lethal effectiveness of the thermal load. It was calculated using the definition of Fphys as the basic equation:

$$Fo(T) = 10^{(\frac{T-Tref}{z})} \cdot \min^{-1} \qquad (25)$$

Where Tref=121° C., and z=10.

Fphys gives the instantaneous rate of Fo. To obtain a cumulative Fo, Fphys has to be integrated over time. Thus, the concept of time must be introduced into the calculations. The time we are interested in is the time an amount of fluid spends at each Tb as the fluid passes down the tube. This time can be calculated by taking into account the changing density of the liquid, and average density within the heat exchanger or simply by using the starting density. The most accurate method would be using the changing density of the fluid to predict the transit time. If continuous equations are used to describe heating and density, the cumulative Fo can be obtained by integration.

To aid in minimizing Fo so that degradation of the pharmaceutical composition is minimized, the coefficient of heat transfer, A, may be calculated for a plurality of flow rates and a plurality of temperatures. Moreover, a sterilized solution may be tested for degradation at a particular Fo value.

It is important to note that the degree of sterilization ($F_o$) for the pharmaceutical composition is preferentially calculated while the pharmaceutical composition is inside and passing through the heat exchanger means. Thus, $F_o$ is calculated in the heat exchanger means.

It is preferred that Fo is substantially continuously calculated (e.g., by a computer) by substantially continuously monitoring temperature and flow rates and recalculating Fo, and adjusting the temperature and/or flow rates if Fo falls below a predetermined level or it or if degradation of the pharmaceutical composition rises above a predetermined level. For example, the flow rate and temperature data may be sent to a computer that constantly calculates Fo based on the data. The calculated Fo values may then be used to adjust the system to obtain the degree of sterilization desired while minimizing degradation of the pharmaceutical composition. The adjustment of the system may be accomplished manually or may be controlled by the computer.

The composition can also be tested for degradation at a particular temperature profile within the heat exchanging-means and at a particular flow rate. Methods of testing for degradation are known to those skilled in the art.

What is claimed is:

1. A method of sterilizing a pharmaceutical composition, the method comprising:

providing a sterilization system including a heat exchanger means for elevating a temperature of a fluid passing therethrough;

providing an adjustable means for flowing a fluid through said sterilization system at a plurality of flow rates;

flowing a fluid through said heat exchanger means of said sterilization system at a fluid flow rate using said adjustable means for flowing;

measuring a first temperature of said fluid at an input of said heat exchanger means, measuring a second temperature of said fluid at an output of said heat exchanger means and measuring a third temperature of said fluid at a point in said heat exchanger means intermediate said input and output of said heat exchanger means, said third temperature being a center tube temperature of said heat exchanger means;

calculating a cumulative degree of sterilization ($F_{cumulative}$) of said fluid using said first, second, and third temperatures of said fluid and said fluid flow rate; and adjusting said heat exchanger means and said adjustable means for flowing responsive to said calculation of said cumulative degree of sterilization ($F_{cumulative}$) to adjust said cumulative degree of sterilization ($F_{cumulative}$) to a predetermined level at which degradation of said fluid in said heat exchanger means of said sterilization system is minimized and at which a predetermined level of sterilization of said fluid is achieved.

2. A method in accordance with claim 1, said method further comprising the step of calculating a coefficient of heat transfer for said sterilization system using said first, second, and third temperatures of said fluid and said flow rate, and wherein said coefficient of heat transfer is used to calculate said cumulative degree of sterilization ($F_{cumulative}$).

3. A method in accordance with claim 1, said method further comprising the steps of periodically measuring said first, second, and third temperatures of said fluid, periodically calculating said cumulative degree of sterilization ($F_{cumulative}$) using said first, second, and third temperatures of said fluid and said fluid flow rate, and periodically adjusting said heat exchanger means and said means for flowing responsive to each said calculation of said cumulative degree of sterilization ($F_{cumulative}$) to adjust said cumulative degree of sterilization ($F_{cumulative}$) to said predetermined level.

4. A method in accordance with claim 1 wherein said cumulative degree of sterilization ($F_{cumulative}$) is calculated using the equation:

$$F_{cumulative} = \int F_o(Tb(t))dt.$$

5. A method of sterilizing a pharmaceutical composition, the method comprising:

providing a sterilization system including a heat exchanger means for elevating a temperature of a fluid passing therethrough;

providing an adjustable means for flowing a fluid through said sterilization system;

flowing a fluid through said heat exchanger means of said sterilization system at a fluid flow rate using said adjustable means for flowing;

periodically measuring a first temperature of said fluid at an input of said heat exchanger means, periodically measuring a second temperature of said fluid at an output of said heat exchanger means, and periodically measuring a third temperature of said fluid at a point in said heat exchanger means intermediate said input and output of said heat exchanger means: said third temperature being a center tube temperature of said heat exchanger means;

periodically calculating a cumulative degree of sterilization ($F_{cumulative}$) of said fluid using said first, second, and third temperatures of said fluid and said fluid flow rate using the equation $F_{cumulative} = \int F_o(Tb(t))dt$ periodically adjusting said heat exchanger means and said means for flowing fluid responsive to each said calculation of said cumulative degree of sterilization ($F_{cumulative}$) in order to adjust said cumulative degree of sterilization ($F_{cumulative}$) to a predetermined level at which degradation of said fluid in said heat exchanger means of said sterilization system is minimized and at which a predetermined level of sterilization of said fluid is achieved.

6. An apparatus for sterilizing a pharmaceutical composition, said apparatus comprising:

a first heat exchanger means for elevating a temperature of a fluid passing therethrough, said first heat exchanger means having an input end and an output end, said first heat exchanger means being adjustable in response to a control signal;

a second heat exchanger means for lowering a temperature of a fluid passing therethrough, said second heat exchanger means in fluid communication with said first heat exchanger means;

an adjustable means for flowing a fluid through said first and second heat exchanger means at a fluid flow rate and for generating a first signal containing said fluid flow rate, said means for flowing being adjustable in response to a control signal;

a means for measuring a first temperature of a fluid at said input end of said first heat exchanger means and for generating a second signal containing said first temperature;

a means for measuring a second temperature of a fluid at said output end of said first heat exchanger means and for generating a third signal containing said second temperature;

a means for measuring a third temperature of a fluid within said first heat exchanger means at a point intermediate said input and output ends and for generating a fourth signal containing said third temperature said means for measuring a third temperature positioned at substantially a center of said heat first exchanger means, said third temperature being a center tube temperature of said first heat exchanger means;

a processing means for calculating a cumulative degree of sterilization ($F_{cumulative}$) of a fluid passing through said first heat exchanger means based upon said fluid flow rate, said first temperature, said second temperature, and said third temperature, for comparing said cumulative degree of sterilization ($F_{cumulative}$) to a predetermined cumulative degree of sterilization, and for generating a control signal for controlling said first heat exchanger means and said adjustable means for flowing;

a means for transferring said first, second, third, and fourth signals to said processing means and for transferring said control signal from said processing means to said first heat exchanger means and said adjustable means for flowing.

7. An apparatus for sterilizing a pharmaceutical composition in accordance with claim 6, wherein said apparatus further comprises a means for measuring a plurality of temperatures of a fluid within said first heat exchanger means at a plurality of points intermediate said input and output ends and for generating a fifth signal containing said plurality of temperatures of a fluid within said first heat exchanger means, wherein said means for transferring is configured to transfer said fifth signal to said processing means, and wherein said processing means calculates ($F_{cumulative}$) based upon said fluid flow rate, said first temperature, said second temperature, said third temperature, and said plurality of temperatures of a fluid within said first heat exchanger means.

8. An apparatus for sterilizing a pharmaceutical composition in accordance with claim 7, wherein said apparatus further comprises a second means for measuring a plurality of temperatures of a fluid within said second heat exchanger means at a plurality of points and for generating a sixth signal containing said plurality of temperatures of a fluid within said second heat exchanger means, wherein said means for transferring transfers said sixth signal to said processing means, and wherein said processing means calculates ($F_{cumulative}$) based upon said fluid flow rate, said first temperature, said second temperature, said third temperature, said plurality of temperatures of a fluid within said first heat exchanger means, and said plurality of temperatures of a fluid within said second heat exchanger means.

* * * * *

UNITED STATES PATENT AND TRADEMARK OFFICE
CERTIFICATE OF CORRECTION

PATENT NO. : 5,603,894
DATED : February 18, 1997
INVENTOR(S) : Alkus, et al

It is certified that error appears in the above-indentified patent and that said Letters Patent is hereby corrected as shown below:

Column 10, line 47, change "means:" to --means,--.

Signed and Sealed this

Seventeenth Day of June, 1997

Attest:

Attesting Officer

BRUCE LEHMAN

Commissioner of Patents and Trademarks